US008465284B2

(12) United States Patent
Craig et al.

(10) Patent No.: US 8,465,284 B2
(45) Date of Patent: Jun. 18, 2013

(54) DENTAL METHODS, COMPOSITIONS, AND KITS INCLUDING ACID-SENSITIVE DYES

(75) Inventors: Bradley D. Craig, Cottage Grove, MN (US); Robert Lee, Lake Elmo, MN (US); Ahmed S. Abuelyaman, Woodbury, MN (US); Afshin Falsafi, Woodbury, MN (US); Steven M. Aasen, Woodbury, MN (US); Joel D. Oxman, Minneapolis, MN (US)

(73) Assignee: 3M Innovative Properties Company, Saint Paul, MN (US)

( * ) Notice: Subject to any disclaimer, the term of this patent is extended or adjusted under 35 U.S.C. 154(b) by 856 days.

(21) Appl. No.: 11/571,762

(22) PCT Filed: Jul. 7, 2005

(86) PCT No.: PCT/US2005/024291
§ 371 (c)(1),
(2), (4) Date: Jan. 8, 2007

(87) PCT Pub. No.: WO2006/014597
PCT Pub. Date: Feb. 9, 2006

(65) Prior Publication Data
US 2008/0299519 A1    Dec. 4, 2008

Related U.S. Application Data

(60) Provisional application No. 60/586,326, filed on Jul. 8, 2004, provisional application No. 60/600,558, filed on Aug. 11, 2004.

(51) Int. Cl.
*A61C 3/00* (2006.01)
*A61C 5/00* (2006.01)
*A61C 5/04* (2006.01)

(52) U.S. Cl.
USPC ............. 433/215; 433/226; 433/9; 433/228.1

(58) Field of Classification Search
USPC ............. 433/9, 228.1, 29, 215–216, 89, 226, 433/8–16, 217.1; 523/115–118; 424/9.7, 424/9.71, 9.8; 106/35
See application file for complete search history.

(56) References Cited

U.S. PATENT DOCUMENTS

| | | |
|---|---|---|
| 3,655,605 A | 4/1972 | Smith |
| 3,797,690 A | 3/1974 | Taylor |
| 4,016,124 A | 4/1977 | Crisp et al. |
| 4,054,598 A | 10/1977 | Blum et al. |
| 4,070,321 A | 1/1978 | Goretta |
| 4,089,830 A | 5/1978 | Tezuka et al. |
| 4,143,018 A | 3/1979 | Crisp et al. |
| 4,204,978 A | 5/1980 | Ibsen et al. |
| 4,259,075 A | 3/1981 | Yamauchi et al. |
| 4,259,117 A | 3/1981 | Yamauchi et al. |
| 4,267,108 A | 5/1981 | Blum et al. |
| 4,298,738 A | 11/1981 | Lechtken et al. |
| 4,302,381 A | 11/1981 | Omura et al. |
| 4,304,734 A | 12/1981 | Jary et al. |
| 4,324,744 A | 4/1982 | Lechtken et al. |
| 4,327,039 A | 4/1982 | Blum et al. |
| 4,342,677 A | 8/1982 | Muramatsu et al. |
| 4,347,233 A | 8/1982 | Yamauchi et al. |
| 4,356,296 A | 10/1982 | Griffith et al. |
| 4,360,605 A | 11/1982 | Schmitt et al. |
| 4,368,403 A | 1/1983 | Lewis |
| 4,376,835 A | 3/1983 | Schmitt et al. |
| 4,383,052 A | 5/1983 | Higo et al. |
| 4,385,109 A | 5/1983 | Lechtken et al. |
| 4,407,761 A | 10/1983 | Blum et al. |
| 4,499,251 A | 2/1985 | Omura et al. |
| 4,503,169 A | 3/1985 | Randklev |
| 4,507,407 A | 3/1985 | Kluger |
| 4,526,728 A | 7/1985 | Finke et al. |
| 4,537,940 A | 8/1985 | Omura et al. |
| 4,539,382 A | 9/1985 | Omura et al. |
| 4,612,384 A | 9/1986 | Omura et al. |
| 4,621,077 A | 11/1986 | Rosini et al. |
| 4,642,126 A | 2/1987 | Zador et al. |
| 4,648,843 A | 3/1987 | Mitra |
| 4,650,847 A | 3/1987 | Omura et al. |
| 4,652,274 A | 3/1987 | Boettcher et al. |
| 4,665,217 A | 5/1987 | Reiners et al. |
| 4,678,436 A | 7/1987 | Kondo |
| 4,687,767 A | 8/1987 | Bosies et al. |
| 4,695,251 A | 9/1987 | Randklev |

(Continued)

FOREIGN PATENT DOCUMENTS

| | | |
|---|---|---|
| DD | 273 846 A1 | 11/1989 |
| DE | 2537463 A1 | 4/1976 |

(Continued)

OTHER PUBLICATIONS

U.S. Appl. No. 60/494,603, filed Aug. 12, 2003, entitled "Dental Compositions and Methods".
Patent Abstracts of Japan, vol. 009, No. 236 (P-390), 9.21.1985 & JP 60 089752A May 20, 1985.
U.S. Appl. No. 60/586,326, filed Jul. 8, 2004, entitled "Dental Methods, Compositions, and Kits Including Acid-sensitive Dyes".
U.S. Appl. No. 60/600,558, filed Aug. 11, 2004 entitled "Dental Methods, Compositions, and Kits Including Acid-sensitive Dyes".
Banerjee et al., *Ind. Eng. Chem. Res.*, vol. 35, No. 9, pp. 3100-3107 "Polymer Precipitation Using a Micellar Nonsolvent: The Role of Surfactant—Polymer Interactions and the Development of a Microencapsulation Technique", (1996).
Buonocore et al., *J. Dent. Res.*, vol. 35, No. 6, pp. 846-851, "A Report on a Resin Composition Capable of Bonding to Human Dentin Surfaces", (1956).
Floyd Green, The Sigma-Aldrich Handbook of Stains, Dyes, & Indicators [with/Transmission Spectrum Reference], Aldrich Chem. Co., Milwaukee, WI (1990).

(Continued)

*Primary Examiner* — Yogesh Patel
(74) *Attorney, Agent, or Firm* — Carlos M. Téllez; 3M Innovative Properties Company

(57) ABSTRACT

Methods and compositions including an aqueous liquid that includes an acid-sensitive dye are disclosed for use in dental and orthodontic procedures. The aqueous liquid can be useful for providing a visible color change to indicate contact with acidic materials including, for example, etching compositions, self-etching adhesives, and self-adhesive compositions.

43 Claims, No Drawings

U.S. PATENT DOCUMENTS

| | | | |
|---|---|---|---|
| 4,710,523 A | 12/1987 | Lechtken et al. |
| 4,719,149 A | 1/1988 | Aasen et al. |
| 4,737,593 A | 4/1988 | Ellrich et al. |
| 4,752,338 A | 6/1988 | Reiners et al. |
| 4,755,620 A | 7/1988 | Iwamoto et al. |
| 4,792,632 A | 12/1988 | Ellrich et al. |
| 4,814,514 A | 3/1989 | Yokota et al. |
| 4,816,495 A | 3/1989 | Blackwell |
| 4,872,936 A | 10/1989 | Engelbrecht |
| 4,922,007 A | 5/1990 | Kieczykowski et al. |
| 4,939,283 A | 7/1990 | Yokota et al. |
| 5,019,651 A | 5/1991 | Kieczykowski |
| 5,026,902 A | 6/1991 | Fock et al. |
| 5,055,497 A | 10/1991 | Okada et al. |
| 5,063,257 A | 11/1991 | Akahane et al. |
| 5,076,844 A | 12/1991 | Fock et al. |
| 5,130,347 A | 7/1992 | Mitra |
| 5,154,762 A | 10/1992 | Mitra et al. |
| 5,172,809 A | 12/1992 | Jacobs et al. |
| 5,180,757 A | 1/1993 | Lucey |
| 5,227,413 A | 7/1993 | Mitra |
| 5,254,198 A | 10/1993 | Kawashima et al. |
| 5,256,447 A | 10/1993 | Oxman et al. |
| 5,324,862 A | 6/1994 | Yokota et al. |
| 5,332,854 A | 7/1994 | Yokota et al. |
| 5,338,769 A | 8/1994 | Miyamoto |
| 5,354,827 A | 10/1994 | Muller et al. |
| 5,367,002 A | 11/1994 | Huang et al. |
| 5,501,727 A | 3/1996 | Wang et al. |
| 5,510,517 A | 4/1996 | Dauer et al. |
| 5,520,725 A | 5/1996 | Kato et al. |
| 5,525,648 A | 6/1996 | Aasen et al. |
| 5,530,038 A | 6/1996 | Yamamoto et al. |
| 5,545,676 A | 8/1996 | Palazzotto et al. |
| 5,554,030 A | 9/1996 | Ario et al. |
| 5,575,645 A | 11/1996 | Jacobs et al. |
| 5,593,303 A | 1/1997 | Cohen et al. |
| 5,608,042 A | 3/1997 | Himeno |
| 5,629,361 A | 5/1997 | Nakabayashi et al. |
| 5,645,429 A | 7/1997 | Blackwell et al. |
| 5,648,491 A | 7/1997 | Dauer et al. |
| 5,658,963 A | 8/1997 | Qian et al. |
| 5,700,875 A | 12/1997 | Zeng et al. |
| 5,710,194 A | 1/1998 | Hammesfahr et al. |
| 5,766,012 A | 6/1998 | Rosembaum et al. |
| 5,834,532 A | 11/1998 | Yamamoto et al. |
| 5,856,373 A | 1/1999 | Kaisaki et al. |
| 5,859,089 A | 1/1999 | Qian |
| 5,871,360 A | 2/1999 | Kato |
| 5,919,836 A | 7/1999 | Reinhardt |
| 5,919,846 A | 7/1999 | Batlaw |
| 5,925,715 A | 7/1999 | Mitra |
| 5,962,550 A | 10/1999 | Akahane et al. |
| 5,965,632 A | 10/1999 | Orlowski et al. |
| 5,980,253 A | 11/1999 | Oxman et al. |
| 5,980,868 A | 11/1999 | Homola |
| 6,004,390 A | 12/1999 | Pflug et al. |
| 6,030,606 A | 2/2000 | Holmes |
| 6,050,815 A | 4/2000 | Adam |
| 6,084,004 A | 7/2000 | Weinmann et al. |
| 6,089,861 A | 7/2000 | Kelly et al. |
| 6,126,922 A | 10/2000 | Rozzi et al. |
| 6,172,131 B1 | 1/2001 | Moszner et al. |
| 6,174,935 B1 | 1/2001 | Matsunae et al. |
| 6,187,833 B1 | 2/2001 | Oxman et al. |
| 6,187,836 B1 | 2/2001 | Oxman et al. |
| 6,213,767 B1 | 4/2001 | Dixon et al. |
| 6,217,644 B1 | 4/2001 | Matsunae |
| 6,251,963 B1 | 6/2001 | Kohler et al. |
| 6,306,926 B1 | 10/2001 | Bretscher et al. |
| 6,309,215 B1 | 10/2001 | Phan et al. |
| 6,331,080 B1 | 12/2001 | Cole et al. |
| 6,350,839 B2 | 2/2002 | Moszner et al. |
| 6,355,704 B1 | 3/2002 | Nakatsuka et al. |
| 6,387,979 B1 | 5/2002 | Hino |
| 6,387,981 B1 | 5/2002 | Zhang et al. |
| 6,387,982 B1 | 5/2002 | Blackwell |
| 6,444,725 B1 * | 9/2002 | Trom et al. .................. 523/118 |
| 6,458,868 B1 | 10/2002 | Okada et al. |
| 6,472,454 B1 | 10/2002 | Qian |
| 6,482,871 B1 | 11/2002 | Aasen et al. |
| 6,506,816 B1 | 1/2003 | Ario et al. |
| 6,528,555 B1 | 3/2003 | Nikutowski et al. |
| 6,565,873 B1 | 5/2003 | Shefer |
| 6,566,413 B1 | 5/2003 | Weinmann et al. |
| 6,572,693 B1 | 6/2003 | Wu et al. |
| 6,575,752 B1 * | 6/2003 | Pflug et al. .................. 433/226 |
| 6,624,236 B1 | 9/2003 | Bissinger et al. |
| 6,669,927 B2 | 12/2003 | Trom et al. |
| 6,691,715 B2 | 2/2004 | Matz et al. |
| 6,765,036 B2 | 7/2004 | Dede et al. |
| 6,765,038 B2 | 7/2004 | Mitra |
| 6,830,450 B2 | 12/2004 | Knopp et al. |
| 6,869,984 B2 | 3/2005 | Kawashima |
| 6,905,672 B2 | 6/2005 | Rajaiah |
| 6,916,858 B2 | 7/2005 | Kojima |
| 6,939,901 B2 | 9/2005 | Nakatsuka |
| 6,960,079 B2 | 11/2005 | Brennan et al. |
| 6,982,288 B2 | 1/2006 | Mitra et al. |
| 6,994,551 B2 | 2/2006 | Wang et al. |
| 7,090,722 B2 | 8/2006 | Budd et al. |
| 7,129,281 B2 * | 10/2006 | Fujiwara ....................... 522/153 |
| 7,134,875 B2 | 11/2006 | Oxman |
| 7,137,812 B2 | 11/2006 | Cleary |
| 7,173,074 B2 | 2/2007 | Mitra et al. |
| 7,186,950 B1 | 3/2007 | Fisher |
| 7,250,452 B2 | 7/2007 | Falsafi |
| 7,262,228 B2 | 8/2007 | Oxman |
| 7,374,420 B2 | 5/2008 | Brennan |
| 7,452,924 B2 | 11/2008 | Aasen et al. |
| 7,473,096 B2 | 1/2009 | Cinader, Jr. |
| 7,541,393 B2 | 6/2009 | Mitra |
| 7,632,098 B2 * | 12/2009 | Falsafi et al. .................. 433/215 |
| 7,699,605 B2 | 4/2010 | Aasen et al. |
| 7,841,464 B2 | 11/2010 | Cinader, Jr. |
| 7,910,632 B2 | 3/2011 | Cinader, Jr. |
| 2001/0044513 A1 | 11/2001 | Moszner et al. |
| 2002/0015682 A1 | 2/2002 | Stangel et al. |
| 2002/0016384 A1 | 2/2002 | Moszner et al. |
| 2002/0061938 A1 * | 5/2002 | Hino ............................ 523/115 |
| 2003/0087986 A1 | 5/2003 | Mitra |
| 2003/0166737 A1 | 9/2003 | Dede et al. |
| 2003/0166740 A1 | 9/2003 | Mitra et al. |
| 2003/0166816 A1 | 9/2003 | Bissinger et al. |
| 2003/0181541 A1 | 9/2003 | Wu et al. |
| 2003/0186196 A1 * | 10/2003 | Wang et al. .................. 433/226 |
| 2003/0187092 A1 | 10/2003 | Fujiwara |
| 2003/0195273 A1 | 10/2003 | Mitra |
| 2003/0196914 A1 * | 10/2003 | Tzou et al. .................... 206/63.5 |
| 2003/0198914 A1 * | 10/2003 | Brennan et al. ................... 433/9 |
| 2004/0110864 A1 | 6/2004 | Hecht |
| 2004/0151691 A1 | 8/2004 | Oxman et al. |
| 2004/0206932 A1 | 10/2004 | Abuelyaman |
| 2005/0074716 A1 | 4/2005 | Cleary et al. |
| 2005/0133384 A1 | 6/2005 | Cinader |
| 2005/0154081 A1 | 7/2005 | Yin |
| 2005/0175965 A1 | 8/2005 | Craig et al. |
| 2005/0175966 A1 | 8/2005 | Falsafi et al. |
| 2005/0176844 A1 * | 8/2005 | Aasen et al. .................. 523/118 |
| 2005/0252413 A1 | 11/2005 | Kangas et al. |
| 2005/0252414 A1 | 11/2005 | Craig et al. |
| 2005/0256223 A1 | 11/2005 | Kolb et al. |
| 2005/0277084 A1 | 12/2005 | Cinader et al. |
| 2006/0030637 A1 | 2/2006 | Mitra |
| 2006/0069181 A1 | 3/2006 | Thalacker |
| 2006/0084026 A1 | 4/2006 | Cinader et al. |
| 2007/0039519 A1 | 2/2007 | Kangas et al. |
| 2007/0207094 A1 | 9/2007 | Oxman |
| 2007/0248927 A1 | 10/2007 | Luchterhandt |
| 2008/0096150 A1 | 4/2008 | Cinader |
| 2008/0299519 A1 | 12/2008 | Craig et al. |
| 2009/0011388 A1 | 1/2009 | Craig |
| 2009/0030101 A1 | 1/2009 | Sang et al. |
| 2009/0075239 A1 | 3/2009 | Abuelyaman |

FOREIGN PATENT DOCUMENTS

| | | |
|---|---|---|
| DE | 35 36076 A1 | 4/1987 |
| DE | 199 18 974 A1 | 12/1999 |
| DE | 695 18 037 T2 | 3/2001 |
| EP | 0 115 812 A2 | 8/1984 |
| EP | 0 173 567 A2 | 3/1986 |
| EP | 0 115 948 B1 | 10/1986 |
| EP | 0 201 031 A2 | 11/1986 |
| EP | 0 237 233 A2 | 9/1987 |
| EP | 237233 A2 | 9/1987 |
| EP | 0 201 778 B1 | 12/1988 |
| EP | 0 184 095 B1 | 7/1989 |
| EP | 323120 | 7/1989 |
| EP | 0 201 031 B1 | 8/1989 |
| EP | 0 206 810 B1 | 4/1990 |
| EP | 0 335 645 B1 | 8/1992 |
| EP | 0 373 384 B1 | 10/1992 |
| EP | 0 537 774 A1 | 4/1993 |
| EP | 0 323 012 B1 | 5/1993 |
| EP | 0 351 076 B1 | 8/1993 |
| EP | 0 712 622 A1 | 5/1996 |
| EP | 0 509 516 B1 | 3/1997 |
| EP | 0 537 774 B1 | 1/1998 |
| EP | 0 897 710 | 2/1999 |
| EP | 0 661 034 B1 | 3/1999 |
| EP | 0 712 622 B1 | 9/1999 |
| EP | 1051961 | 11/2000 |
| EP | 1051961 A1 | 11/2000 |
| EP | 1121924 A2 | 8/2001 |
| EP | 1 141 094 | 7/2002 |
| EP | 1 287 805 A1 | 3/2003 |
| EP | 1 346 717 A1 | 9/2003 |
| GB | 2 251 861 A | 7/1992 |
| JP | 59015468 | 1/1984 |
| JP | 59-135272 | 8/1984 |
| JP | 60-089752 | 5/1985 |
| JP | 61-151104 | 7/1986 |
| JP | 06-041162 | 2/1994 |
| JP | 7330530 | 12/1995 |
| JP | 10-512567 | 12/1998 |
| JP | 11139920 | 5/1999 |
| JP | 2000204010 | 7/2000 |
| JP | 2001072936 | 3/2001 |
| JP | 2004182661 | 7/2004 |
| JP | 2005-008537 | 1/2005 |
| WO | WO 98/03443 | 1/1998 |
| WO | WO 98/46198 A1 | 10/1998 |
| WO | WO 00/30591 A1 | 6/2000 |
| WO | WO 00/38619 A2 | 7/2000 |
| WO | WO 00/38619 A3 | 7/2000 |
| WO | WO 00/42092 A1 | 7/2000 |
| WO | WO 01/07444 A1 | 2/2001 |
| WO | WO 01/30304 | 5/2001 |
| WO | WO 01/30305 A1 | 5/2001 |
| WO | WO 01/30306 A1 | 5/2001 |
| WO | WO 01/30307 A1 | 5/2001 |
| WO | WO 0138449 | 5/2001 |
| WO | WO 01/92271 A1 | 12/2001 |
| WO | WO 02/02057 | 1/2002 |
| WO | WO 02/11642 | 2/2002 |
| WO | WO 02/092021 A1 | 11/2002 |
| WO | WO 03/013444 A1 | 2/2003 |
| WO | WO 03/063804 A1 | 8/2003 |
| WO | WO 03/068174 A1 | 8/2003 |
| WO | WO 2005/004819 A | 1/2005 |
| WO | WO 2005/018581 A | 3/2005 |
| WO | WO 2006/014597 | 2/2006 |
| WO | WO 2006/020760 | 2/2006 |
| WO | WO 2007-075666 | 7/2007 |

OTHER PUBLICATIONS

Holmberg et al., "Microemulsions," Chapter 6, *Surfactants and Polymers in Aqueous Solution*, Second Edition, John Wiley & Sons, pp. 138-155 (2003; Reprinted with corrections in 2004).
ISO Standard 4049:2000.
ISO Standard 7489.
ISO Standard 9917-1:2003.
Leung et al., "Ch. 9, Microemulsions: Formation, Structure, Properties, and Novel Applications," *Surfactants in Chemical/Processing Engineering*, Marcel Dekker, Inc., New York and Basel, Title page, Publication page, and pp. 315-367(1988).
Ostrovosky et al., "Mechanism of Microemulsion Formation in Systems with Low Interfacial Tension: Occurence, Properties, and Behavior of Microemulsions," *Journal of Colloid and Interface Science*, 102(1): 206-226 (Nov. 1984).
Overbeek et al., "Microemulsions," in *Surfactants*, Th. F. Thadros, Ed., Academic Press, London, Title Page, Table of Contents, pp. 111-132 (1984).
Ruckenstein et al., "Stability of Microemulsions," *J. Chem. Soc. Faraday Trans II*, vol. 71; pp. 1690-1707 (1975).
Rumphorst, et al. "Examination of the Formulation of an Innovative Single-Component Bonding System," *Signature*, vol. 6, No. 1, pp. 1-3 (Sep. 2000).
Safran et al., "Phase Diagrams for Microemulsions," *Physical Review Letters*, vol. 50, No. 24, pp. 1930-1933 (Jun. 13, 1983).
Xu et al., *J. Phys. Chem.*, 97:11350-11353 (1993).
U.S. Appl. No. 10/729,497, filed Dec. 5, 2003, entitled "Compositions Including Polymerizable Bisphosphonic Acids and Methods".
U.S. Appl. No. 60/600,658, filed Aug. 11, 2004, entitled "Self-adhesive Compositions Including a Plurality of Acidic Compounds".
Dyba et al., J. Chem. Soc., "1-Hydroxyalkane-1,1-diyldiphosphonates as potent chelating agents for metal ions. Potentiometric and spectroscopic studies of copper(II) coordination" Dalton Trans. (1996), 1119-1123.
Gumienna-Kontecka et al., J. Inorg. Biochem., Bisphosphonate chelating agents Coordination ability of 1-phenyl-1-hydroxymethylene bisphosphonate towards $Cu^{2+}$ ions, 89 (2002), 13-17.
Kieczykowski et al., J. Org. Chem., "Preparation of (4-Amino-1-Hydroxybutylidene) bisphosphonic Acid Sodium Salt, MK-217 (Alendronate Sodium). An Improved Procedure for the Preparation of 1-Hydroxy-1,1-bisphosphonic Acids," (1995), 60, 8310-8312.
Mathis et al., Dental Materials, "Properties of a New Glass Ionomer/Composite Resin Hybrid Restorative," Table of Contents, pp. 355-358.
Mathis et al., Journal of Dental Research, "Properties of a New Glass Ionomer/Composite Resin Hybrid Restorative," Abstract No. 51, vol. 66, pp. 113 (1987).
Moszner et al., Macromol. Chem. "Monomers for adhevise polymers, $2^u$, Synthesis and radical polymerisation of hydrolytically stable acrylic phosphonic acids" Phys. 200 (1999), 1062-67.
Technical Product Profile, "3M ESPE Adper™ Prompt™ L-Pop™ and Adper™ Prompt™ Self-Etch adhesives," Title page, Table of Contents, and pp. 3, 5-23, and Publication Page, 3M IPC (2002).
Tromelin et al., "Cetophosphonates Et Esters Cycliques D'Hydroxymethylenes Diphosphonates Syntheses, Structures Et Hydrolyse," Phosphorus Sufur Relat. Elem. 27, (1986), pp. 301-312.
Palma, R.G.; Turbino, M.L.; Watson, E.; Powers, J.M.: "Bond Strength to dentin with artificial carious lesions: influence of caries detecting dye" American Journal of Dentistry, vol. 11, No. 3, 1998, pp. 128-130, XP008055059 abstract.
Kazemi, R.B.; Meiers, J.C.; Peppers, K: "Effect of caries desclosing agents on bond strengths of total-etch and self-etching primer dentin bonding systems to resin composite" Operative Dentistry, vol. 27, No. 3, 2002, pp. 238-242, XP008054961, whole document.
TYRIAN™ SPE Universal Self-Priming Etchant, TYRIAN SPE General Information, BISCO, Inc., Schaumburg, IL [retrieved from the internet on Jul. 7, 2004] URL http://www.bisco.com/instructions/tyrianspe_instr_print.asp 8 pages.
Hodges et al., Journal of Orthodontics, "Unusual Indelible Enamel Staining Following Fixed Appliance Treatment", vol. 27, pp. 303-306 (2000).
Written Opinion of ISR for PCT/US2005/024291.
Written Opinion of ISR for PCT/US2004/025936.
IPER for PCT/US03/41487.
Written Opinion of ISR for PCT/US2005/028536.
Alberti, "Cationic Dyes for Acrylic Fibers IV. Catonic Dyes from 6-Methyl-2-(p-Aminophenyl) Benzothiazole and Angular 2-Aminonapthtothiazoles", Chimica e L'Industria, 1974, vol. 56, No. 10, pp. 684-686.
Billmeyer, Principles of Color Technology, Second Edition, New York, NY (1981).

"Blue No. 403", [online], [retrieved from the internet on Aug. 24, 2006], <http://www02.so-net.ne.jp/~tombo/ci/b403e.htm>, 1 page.

Clinpro Sealant, Technical Product Profile, No. 70/2009-2265-9, 3M ESPE, (2001), pp. 1-20.

"Color Center, Color Handbook, Anthrapyrimidine", Special Chem Innovations and Solutions [on line], [retrieved from the internet on Aug. 24, 2006], <http://www.specialchem4coatings.com/tc/color-handbook>, 2 pages.

"Colour Index", The Society of Dyers and Colourists [on line], [retrieved from the internet on Nov. 29, 2005], <http://www.sdc.org.uk/publications/ci4classes.htm>, 2 pages.

"Disperse Dyes", Technology Information Forecasting and Assessment Council, Asian and Pacific Centre for Transfer of Technology, [on line], [retrieved from the internet on Nov. 28, 2005], <http://www.tifac.org.in/offer/tsw/apctt10.htm>, 4 pages.

"Dye Classes for Principal Applications," Dr. Klaus Hunger (author and editor), Wiley Interscience Online Book, [retrieved from the internet on Nov. 29, 2005], <http://www.3.interscience.wiley.com/cgi-bin/summary/107642439/SUMMARY>, 3 pages.

"Epochem Products 2004", Epochem Co., Ltd, <http://www.Epochem.com>, 2002-2004, pp. 1-25.

"Essay: Dyes and Dyeing", Supplement to Experiment 9, Univ. of CO, Boulder, Dept. of Chem. and Biochem. 2006, pp. 63-70.

Freeman, "Synthetic Dyes Based on Toxicological Considerations", National Textile Center Annual Report, Sep. 1993, pp. 167-176.

Green, The Sigma-Aldrich Handbook of Stains, Dyes, and Indicators, Aldrich Chemical Company, pp. 284, 290, 291, 398, 647, 660, (1990).

Heitzman, "Organic Yellows for Plastics", Sun Chemical Corporation, Performance Plastics Business Unit, pp. 12-15.

"ONE-UP Bond F" literature, Tokuyama Corp., Product description and general information, 1 page, [date unknown but believed to be prior to the date of the filing of the present application].

Patel, "Synthesis of Monoazo Disperse Dyes from 2-Amino-4-Methylbenzothiazole and Their Application on Polyester Fiber", Oriental Journal Chemistry, 1996, vol. 12, No. 2, pp. 193-195.

StainsFile, "Anthraquinone Dyes", [retrieved from the internet on Nov. 28, 2005], <http://stasfile.info.StainsFile/dyes/class/clsanthq.htm>, 1 page.

The Complete Technology Book on Dyes & Dye Intermediates, National Institute of Industrial Research [on line], [retrieved from the internet on Nov. 29, 2005], <http://www.niir.org>, pp. 1-42. [ISBN: 81-86623-79-5].

Twenty-first Report of the Interagency Testing Committee to the Administrator; Receipt of Report and Request for Comments Regarding Priority List of Chemicals, Notices, Federal Register, vol. 52, No. 224, Nov. 1987, pp. 44830-44837.

International Search Report for Int'l Appln. No. PCT/US2003/041487, 3 pages.

International Search Report for Int'l Appln. No. PCT/US2004/025936, 3 pages.

International Search Report for Int'l Appln. No. PCT/US2005/024291, 4 pages.

International Search Report for Int'l Appln. No. PCT/US2005/028536, 4 pages.

International Search Report for Int'l Appln. No. PCT/US2007/087192, 3 pages.

* cited by examiner

… (1) …

DENTAL METHODS, COMPOSITIONS, AND KITS INCLUDING ACID-SENSITIVE DYES

CROSS REFERENCE TO RELATED APPLICATIONS

This application is a national stage filing under 35 U.S.C. 371 of PCT/US 2005/024291 filed Jul. 7, 2005, which claims the benefit of U.S. Provisional Application No. 60/586,326, filed Jul. 8, 2004, and U.S. Provisional Application No. 60/600,558, filed Aug. 11, 2004, the disclosures of which are incorporated by reference in their entirety herein.

BACKGROUND

For a variety of dental procedures, it is important, but often difficult, for a practitioner to be able to detect materials and surfaces that have come in contact with acidic materials. For example, etching compositions are acidic materials that are routinely applied to a surface of a dental structure as part of a variety of bonding procedures, and it is important for the practitioner to be able to readily determine which surfaces have had an etching composition applied thereto. However, it is oftentimes difficult for the practitioner to visually detect which surfaces have had an etchant applied thereto.

Recent advances in dentistry have provided dental adhesives and compositions that are self-etching and thus, do not require a separate etching step. Some of these self-etching adhesives and compositions may be, and even preferably are, applied to a wet surface of a dental structure. In some cases it may be difficult to determine which surfaces have been properly wetted before application of the self-etching adhesive or composition. In some cases, the surface of the dental structure will not be properly etched if the surface was not properly wetted before application of the self-etching adhesive or composition.

There exists a need for methods and compositions to visually indicate surfaces and materials that are contacted with acidic materials.

SUMMARY OF THE INVENTION

In one aspect, the present invention provides a method for applying an etching composition to a dental structure. The method includes: wetting a surface of a dental structure with a liquid including an acid-sensitive dye and water; and applying an etching composition to at least a portion of the wet dental structure surface under conditions effective to cause a visually observable color change in the portion of the dental structure surface having the etching composition applied thereon.

In another aspect, the present invention provides a method for applying a self-etching adhesive to a dental structure. The method includes: wetting a surface of a dental structure with a liquid including an acid-sensitive dye and water; and applying a self-etching adhesive to at least a portion of the wet dental structure surface under conditions effective to cause a visually observable color change in the portion of the dental structure surface having the self-etching adhesive applied thereon. Preferably, the visually observable color change is from colored to essentially colorless.

In another aspect, the present invention provides a method for applying a self-adhesive composition to a dental structure. The method includes: wetting a surface of a dental structure with a liquid including an acid-sensitive dye and water; and applying a self-adhesive composition to at least a portion of the wet dental structure surface under conditions effective to cause a visually observable color change in the portion of the dental structure surface having the self-adhesive composition applied thereon. Preferably, the visually observable color change is from colored to essentially colorless.

Optionally, the self-adhesive composition can be provided as a precoated orthodontic appliance by a manufacturer, and the precoated orthodontic appliance can be applied to the wet dental structure surface. Exemplary orthodontic appliances include, for example, brackets, buccal tubes, bands, cleats, buttons, lingual retainers, bite blockers, and combinations thereof.

Alternatively, the self-adhesive composition can be applied to a surface of an orthodontic appliance by a practitioner to provide a coated orthodontic appliance, and the coated orthodontic appliance can be applied to the wet dental structure surface. Optionally, the self-adhesive composition can be provided on an adhesive transfer area of a substrate, and the self-adhesive composition can be transferred from the adhesive transfer area of the substrate for applying to the orthodontic appliance.

In another aspect, the present invention provides a method of bonding a dental material to a dental structure. The method includes: wetting a surface of a dental structure with a liquid including an acid-sensitive dye and water; applying a self-etching adhesive to at least a portion of the wet dental structure surface under conditions effective to cause a visually observable color change in the portion of the dental structure surface having the self-etching adhesive applied thereon; drying the dental structure surface to form a first adhesive layer thereon; optionally applying a second adhesive over the first layer to form a second adhesive layer thereon; applying a dental material to the dental structure surface having the first adhesive layer and optionally the second adhesive layer thereon; and hardening at least one of the adhesive layers under conditions effective to form a bond between the dental material and the dental structure. Preferably, the visually observable color change is from colored to essentially colorless. Preferably, the adhesive is hardened under conditions effective to form a bond between the dental material and the dental structure of at least 7 MPa. The adhesive can be hardened before, during, or after applying the dental material. The second adhesive can be the same as the self-etching adhesive or different than the self-etching adhesive. The dental material can include, for example, a dental restorative, an orthodontic adhesive, or an orthodontic appliance.

In another aspect, the present invention provides a method of restoring a dental structure. The method includes: wetting a surface of a dental structure with a liquid including an acid-sensitive dye and water; applying a self-adhesive composition to at least a portion of the wet dental structure surface under conditions effective to cause a visually observable color change in the portion of the dental structure surface having the self-adhesive composition applied thereon; and hardening the self-adhesive composition under conditions effective to form a bond between the hardened composition and the dental structure of at least 7 MPa. Preferably, the self-adhesive composition includes at least 40% by weight filler. Preferably, the visually observable color change is from colored to essentially colorless.

In another aspect, the present invention provides a method of adhering an orthodontic appliance to a tooth. In one embodiment, the method includes: wetting a surface of a tooth with a liquid including an acid-sensitive dye and water; applying a self-adhesive composition to at least a portion of the wet tooth surface under conditions effective to cause a visually observable color change in the portion of the tooth surface having the self-adhesive composition applied thereon; applying an orthodontic appliance to the tooth surface having the self-adhesive composition applied thereon; and hardening the self-adhesive composition under conditions effective to form a bond between the orthodontic appliance and the tooth.

In another embodiment, the method includes: wetting a surface of a tooth with a liquid including an acid-sensitive dye and water; applying an orthodontic appliance having a self-adhesive composition thereon to at least a portion of the wet tooth surface under conditions effective to cause a visually observable color change in the portion of the tooth surface having the orthodontic appliance and self-adhesive composition applied thereon; and hardening the self-adhesive composition under conditions effective to form a bond between the orthodontic appliance and the tooth. In some embodiments, the method further includes applying a self-adhesive composition to an orthodontic appliance to provide the orthodontic appliance having the self-adhesive composition thereon. In other embodiments, the orthodontic appliance having the self-adhesive composition thereon is provided as a precoated orthodontic appliance.

In another aspect, the present invention provides a multi-part dental composition including: a first part including an acid-sensitive dye; and a second part including an acid, wherein contacting the first part and the second part is effective to cause a color change.

In another aspect, the present invention provides a method for using a multi-part dental composition including contacting a first part including an acid-sensitive dye and a second part including an acid, wherein contacting is effective to cause a color change. Preferably, the color change is from colored to essentially colorless. Optionally, the second part includes a self-etching adhesive or a self-adhesive composition.

In another aspect, the present invention provides kits that include an acid-sensitive dye. In one embodiment, the kit includes: a liquid including an acid-sensitive dye and water; and a dental etching composition. In another embodiment, the kit includes: a liquid including an acid-sensitive dye and water; and a self-etching dental adhesive. In another embodiment, the kit includes: a liquid including an acid-sensitive dye and water; and a self-adhesive dental composition.

Definitions

As used herein, "adhesive" or "dental adhesive" refers to a composition used as a pre-treatment on a dental structure (e.g., a tooth) to adhere a "dental material" (e.g., "restorative," an orthodontic appliance (e.g., bracket), or an "orthodontic adhesive") to the dental structure. An "orthodontic adhesive" refers to a highly (generally greater than 40% by weight) filled composition (more analogous to a "restorative material" than to a "dental adhesive") used to adhere an orthodontic appliance to a surface of a dental structure (e.g., tooth). Generally, the surface of the dental structure is pre-treated, e.g., by etching, priming, and/or applying an adhesive to enhance the adhesion of the "orthodontic adhesive" to the dental structure.

As used herein, a "restorative" or a "dental restorative" are used interchangeably and include, for example, cured or uncured composites such as glass ionomer cements and modified glass ionomer cements, fillings, sealants, inlays, onlays, crowns, bridges, and combinations thereof.

As used herein, a "filling" refers to a highly filled paste suitable for filling a substantial void in a tooth structure.

As used herein, a "non-aqueous" composition (e.g., an adhesive) refers to a composition in which water has not been added as a component. However, there may be adventitious water in other components of the composition, but the total amount of water does not adversely affect stability (e.g., the shelf-life) of the non-aqueous composition. Non-aqueous compositions preferably include less than 1% by weight, more preferably less than 0.5% by weight, and most preferably less than 0.1% by weight water, based on the total weight of the non-aqueous composition.

As used herein, a "self-etching" composition refers to a composition that bonds to a dental structure without pretreating the surface of the dental structure surface with an etchant. Preferably, a self-etching composition can also function as a self-primer wherein no separate etchant or primer are used.

As used herein, a "self-adhesive" composition refers to a composition that is capable of bonding to a dental structure without pretreating the surface of the dental structure with a primer or bonding agent. Preferably, a self-adhesive composition is also a self-etching composition wherein no separate etchant is used.

As used herein, "hardening" or "curing" a composition are used interchangeably and refer to polymerization and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental structure" refers to tooth structures (e.g., enamel, dentin, and cementum) and bone. As used herein, a "dental structure surface" or a "tooth surface" refers to an exposed surface of a dental structure or a tooth, respectively. The exposed surface may optionally include a material (e.g., a layer of material) on the dental structure or tooth.

As used herein, an "uncut" dental structure surface refers to a dental structure surface that has not been prepared by cutting, grinding, drilling, etc.

As used herein, an "unetched" dental structure surface refers to a tooth or bone surface that has not been treated with an etchant prior to application of a self-etching adhesive or a self-adhesive compositions of the present invention.

As used herein, an "etchant" refers to an acidic composition that is capable of fully or partially solubilizing (i.e., etching) a dental structure surface. The etching effect can be visible to the naked human eye and/or instrumentally detectably (e.g., by light microscopy). Typically, an etchant is applied to the dental structure surface for a period of about 10 to 30 seconds.

As used herein, a "wet" dental structure surface refers to a surface of a dental structure that has visible water present (i.e., visible to a naked human eye).

As used herein, a "dry" dental structure surface refers to a surface of a dental structure that has been dried (e.g., air dried) and does not have present visible water.

As used herein, "dental material" refers to a material that may be bonded to a dental structure and includes, for example, dental restoratives, orthodontic appliances, and/or orthodontic adhesives.

As used herein, a "surfactant" refers to a surface-active agent that modifies the nature of a surface (e.g., reduces the surface tension) and encompasses surface-active agents typically referred to as "wetting agents."

As used herein, "a" or "an" means "at least one" or "one or more" unless otherwise indicated.

DETAILED DESCRIPTION OF PREFERRED EMBODIMENTS

In one exemplary embodiment, the present invention provides methods and compositions to visually indicate (or identify) a dental structure surface that has been contacted with an aqueous liquid, and further to visually indicate when that wet surface has been subsequently contacted with an acidic dental composition. Such results can be achieved by including an acid-sensitive dye in the aqueous liquid.

In other exemplary embodiments, the invention provides an acid-sensitive dye to indicate when components of a multi-component dental composition have been contacted or mixed. For example, one component (e.g., an aqueous liquid component) of a multi-component dental composition may include an acid-sensitive dye to visually indicate when that component has been contacted or mixed with another component or components of the multi-component dental composition.

Acid-sensitive dyes useful in the present invention are dyes that exhibit different colors (or lack of color) at different pH conditions. Useful acid-sensitive dyes include, for example, well-known pH indicator dyes. Typically, such dyes are of low toxicity and are miscible or dispersable in liquids, preferably aqueous liquids (i.e., liquids that include water, preferably as the major component). Preferably such dyes are soluble in aqueous liquids, and more preferably form stable aqueous solutions.

Suitable acid-sensitive dyes useful in the present invention are well known to one of skill in the art and include, for example, Eosin dyes (e.g., Rose Bengal, Bromothymol Blue, Erythrosin B, and Eosin Y), azo dyes (Methyl Red and Methyl Orange), triarylmethane dyes, oxonol dyes, and phenolphthalein. Useful acid-sensitive dyes are frequently commercially available. See, for example, Floyd J. Green, *The Sigma-Aldrich Handbook of Stains, Dyes, and Indicators [with Transmission Spectrum Reference]*, Aldrich Chemical Co., Milwaukee, Wis. (1990) for exemplary acid-sensitive dyes. Exemplary preferred acid-sensitive dyes include Rose Bengal, Bromothymol Blue, Methyl Red, and Methyl Orange. A more preferred acid-sensitive dye is Rose Bengal.

Methods and compositions of the present invention include liquids that include an acid-sensitive dye and water (i.e., aqueous liquids). Preferably the acid-sensitive dye is dissolved in the aqueous liquid, thereby forming a solution of the acid-sensitive dye in the aqueous liquid. Preferably, the aqueous liquid includes at least 0.0001% by weight, more preferably at least 0.001% by weight, and most preferably at least 0.01% by weight, of an acid-sensitive dye, based on the total weight of the aqueous liquid. Preferably, the aqueous liquid includes at most 5% by weight, more preferably at most 2% by weight, and most preferably at most 1% by weight acid-sensitive dye, based on the total weight of the aqueous liquid.

Aqueous liquids including an acid-sensitive dye useful in the present invention exhibit at least one visually observable color change when the pH of the aqueous liquid is changed. Preferably, the aqueous liquids exhibit a visually observable color change when the pH of the aqueous liquid is changed to become more acidic. For certain specific embodiments (e.g., embodiments that include applying an etching composition to a dental structure), the aqueous liquid preferably exhibits a visually observable color change when the pH is changed from a pH greater than or equal to 5 to a pH less than or equal to 3.

The term "visually observable color change" is meant to include a change in color from colored to essentially colorless, a change in color from essentially colorless to colored, or a change from a first color to a second color, that is observable by a naked eye of a human observer under ordinary office lighting conditions. Preferably, a visually observable color change corresponds to a change in CIELAB color coordinates $\Delta E$ units of at least 10, more preferably at least 20, and most preferably at least 30.

In addition to an acid-sensitive dye, aqueous liquids useful in the present invention can also optionally include stabilizers, buffers, surfactants, antibacterial agents, water-soluble monomers (e.g., polymerizable components), pH adjuster agents, thickeners, fluoride anions, fluoride releasing agents, and combinations thereof. In certain embodiments, an aqueous liquid including an acid-sensitive dye is applied to a dental structure in such a manner to impart a first color to the structure. Upon subsequent application of an acidic material (e.g., a dental etchant, a dental self-etching adhesive, or a dental self-adhesive composition) to the wet structure, the pH of the initially applied aqueous liquid including the acid-sensitive dye is lowered, thereby imparting a second color to the structure. Preferably, the first color is readily visible to an observer (e.g., a red, pink, orange, or blue color), whereas the second color is essentially colorless. As used herein, "essentially colorless" means that no color difference between the dental structure and the dental structure having the aqueous liquid applied thereto is observable by a naked eye of a human observer under ordinary office lighting conditions. Preferably, "essentially colorless" corresponds to a color difference between the dental structure and the dental structure having the aqueous liquid applied thereto in CIELAB color coordinates $\Delta E$ units of at most 10, more preferably at most 6, and most preferably at most 3. At the end of the procedure, it is typically desirable that the dental structure remains essentially colorless, i.e, that no visually observable color returns to the dental structure surface over time.

Preferred acid-sensitive dyes are those that exhibit a color change from a first color (not essentially colorless) to essentially colorless (and more preferably colorless) upon lowering of the pH.

Self-Etching Adhesives

Self-etching adhesives refer to adhesives that bond to a dental structure without pretreating the surface of the dental structure surface with an etchant. Preferably, a self-etching adhesive can also function as a self-primer wherein no separate etchant or primer are used. Self-etching adhesives are well known to those of skill in the art and include, for example, those disclosed in U.S. Pat. No. 6,506,816 (Ario et al.); U.S. Pat. Application Publication No. 2004/0206932 A1 (Abuelyaman); U.S. patent application Ser. No. 10/916,168, filed Aug. 11, 2004; and U.S. patent application Ser. No. 10/916,169, filed Aug. 11, 2004. Exemplary self-etching adhesives also include those available under the trade designation ADPER PROMPT L-POP from 3M ESPE (St. Paul, Minn.).

In one exemplary embodiment, the self-etching adhesive is a non-aqueous self-etching adhesive. The non-aqueous self-etching adhesive can include, for example, an ethylenically unsaturated compound with acid functionality, an ethylenically unsaturated compound without acid functionality, and an initiator system. Exemplary acid-functionality includes carboxylic acid functionality includes phosphoric acid functionality, phosphonic acid functionality, sulfonic acid functionality, or combinations thereof. Optionally, the non-aqueous self-etching adhesive further includes a filler. Optionally, the non-aqueous self-etching adhesive further includes a surfactant. Exemplary non-aqueous self-etching adhesives are disclosed, for example, in U.S. patent application Ser. No. 10/916,168, filed Aug. 11, 2004.

In another exemplary embodiment, the self-etching adhesive includes a water-in-oil emulsion (e.g., a microemulsion). Preferably, the emulsion is physically and/or chemically stable. The self-etching adhesive can include, for example, an ethylenically unsaturated compound with acid functionality, an ethylenically unsaturated compound without acid functionality, an initiator system, and water. In some embodiments, the self-etching adhesive includes less than 30% by weight water. Exemplary acid-functionality includes carboxylic acid functionality includes phosphoric acid functionality, phosphonic acid functionality, sulfonic acid functionality, or combinations thereof. Optionally, the self-etching adhesive further includes a filler. Optionally, the self-etching adhesive further includes a surfactant. Exemplary self-etching adhesives including a water-in-oil emulsion are disclosed, for example, in U.S. patent application Ser. No. 10/916,169, filed Aug. 11, 2004.

Self-Adhesive Compositions

Self-adhesive compositions refer to compositions that are capable of bonding to a dental structure without pretreating the surface of the dental structure with a primer or bonding agent. Preferably, a self-adhesive composition is also a self-etching composition wherein no separate etchant is used. Self-adhesive compositions are known to those of skill in the art and include, for example, those disclosed in U.S. Pat. Application Publication No. 2004/0110864 A1 (Hecht et al.) and U.S. patent application Ser. No. 10/916,240, filed Aug. 11, 2004.

In one exemplary embodiment, the self-adhesive composition is a non-aqueous self-adhesive composition. The non-aqueous self-adhesive composition can include, for example, an ethylenically unsaturated compound with acid functionality, an ethylenically unsaturated compound without acid functionality, an initiator system, and at least 40% by weight filler, based on the total weight of the non-aqueous self-adhesive composition. Exemplary acid functionality includes, for example, carboxylic acid functionality, phosphoric acid functionality, phosphonic acid functionality, sulfonic acid functionality, or combinations thereof. Optionally, the non-aqueous self-adhesive composition further includes a surfactant. Exemplary non-aqueous self-adhesive compositions are disclosed, for example, in U.S. patent application Ser. No. 10/916,240, filed Aug. 11, 2004.

Methods, Compositions, and Kits

Aqueous liquids including an acid-sensitive dye as described herein are particularly useful in aiding the practitioner to determine whether a surface of a dental structure has been properly wetted before application of a self-etching adhesive or self-adhesive composition thereto.

For example, a surface of a dental structure can be wetted with a liquid including an acid-sensitive dye and water prior to applying an etching composition, a self-etching adhesive, or a self-adhesive composition to at least a portion of the wet dental structure surface. The application of the etching composition, self-etching adhesive, or self-adhesive composition can cause a visually observable color change in the portion of the dental structure surface having the etching composition, self-etching adhesive, or self-adhesive composition applied thereon. Preferably, the visually observable color change is from colored to essentially colorless.

Optionally, a self-adhesive composition can be provided by a manufacturer as a precoated orthodontic appliance appliance that is packaged in a suitable container, and the precoated orthodontic appliance can be applied by a practitioner to the wet dental structure surface. Exemplary orthodontic appliances include, for example, brackets, buccal tubes, bands, cleats, buttons, lingual retainers, bite blockers, and combinations thereof. Exemplary containers are well known in the art and are disclosed, for example, in U.S. Pat. Nos. 5,172,809 (Jacobs et al.), 6,089,861 (Kelly et al.) and U.S. Pat. Application Publication No. 2003/0196914 A1 (Tzou et al.).

Alternatively, a self-adhesive composition can be applied to a surface of an orthodontic appliance by a practitioner to provide a coated orthodontic appliance, and the coated orthodontic appliance can be applied to the wet dental structure surface. Optionally, the self-adhesive composition can be provided on an adhesive transfer area of a substrate, and the self-adhesive composition can be transferred from the adhesive transfer area of the substrate for applying to the orthodontic appliance. Exemplary substrates with transfer areas are described, for example, in U.S. Pat. No. 6,213,767 (Dixon et al.).

Further, the present invention can be useful for bonding a dental material to a dental structure. For example, a surface of a dental structure can be wetted with a liquid including an acid-sensitive dye and water prior to applying a self-etching adhesive to at least a portion of the wet dental structure surface. The application of the self-etching adhesive can cause a visually observable color change in the portion of the dental structure surface having the self-etching adhesive applied thereon. Preferably, the visually observable color change is from colored to essentially colorless. The dental structure surface can be dried to form a first adhesive layer thereon. Optionally a second adhesive can be applied over the first layer to form a second adhesive layer thereon. The second adhesive can be the same as the self-etching adhesive or different than the self-etching adhesive. Finally, a dental material can be applied to the dental structure surface having the first adhesive layer and optionally the second adhesive layer thereon. The dental material can include, for example, a dental restorative, an orthodontic adhesive, or an orthodontic appliance. At least one of the adhesive layers can be hardened under conditions effective to form a bond between the dental material and the dental structure. The adhesive can be hardened before, during, or after applying the dental material. Preferably, the adhesive is hardened under conditions effective to form a bond between the dental material and the dental structure of at least 7 MPa.

Further, the present invention can be useful for restoring a dental structure. For example, a surface of a dental structure can be, wetted with a liquid including an acid-sensitive dye and water prior to applying a self-adhesive composition to at least a portion of the wet dental structure surface. Preferably, the self-adhesive composition includes at least 40% by weight filler. The application of the self-adhesive composition can cause a visually observable color change in the portion of the dental structure surface having the self-adhesive composition applied thereon. Preferably, the visually observable color change is from colored to essentially colorless. The self-adhesive composition can be hardened under conditions effective to form a bond between the hardened composition and the dental structure of at least 7 MPa.

Further, the present invention can be useful for adhering an orthodontic appliance to a tooth. For example, a surface of a tooth can be wetted with a liquid including an acid-sensitive dye and water prior to applying a self-adhesive composition and an orthodontic appliance to at least a portion of the wet tooth surface. In some embodiments, the self-adhesive composition alone is applied to the wet tooth surface. In other embodiments, an orthodontic appliance having the self-adhesive composition thereon is applied to the wet tooth surface. Optionally, the orthodontic appliance having the self-adhesive composition thereon can be provided as a precoated orthodontic appliance. As an additional option, the self-adhesive composition can be applied to an adhesive that has been previously coated onto the base of an appliance and previously hardened to form a custom bonding pad or base having a contour that precisely matches the contour of the patient's tooth. The application of the self-adhesive composition can cause a visually observable color change in the portion of the tooth surface having the self-adhesive composition applied thereon. The self-adhesive composition can be hardened under conditions effective to form a bond between the orthodontic appliance and the tooth.

As yet another option, the self-adhesive composition is applied during an orthodontic bonding procedure using a transfer tray such as the custom transfer apparatus described in U.S. patent application Ser. No. 10/967,797, filed Oct. 18, 2004. In this option, the surface of the patient's teeth are first wetted with a liquid including an acid-sensitive dye and water. Next, a transfer tray having the self-adhesive composition applied to selected areas of the tray is placed over the patient's teeth, with the result that the self-adhesive composition is transferred to corresponding areas of the patient's teeth. In this embodiment, the self-adhesive composition is a self-etching primer, and the resultant color change provides visual confirmation that the primer has been applied to the selected areas of the patient's teeth. An orthodontic appliance is then bonded to the selected area of each tooth. Preferably, the orthodontic appliance is a precoated appliance. Optionally, the appliances are placed on the tooth surfaces in an indirect bonding procedure using, for example, the placement device described in U.S. Pat. Application Publication No. 2005/0074716 (Cleary et. al).

Aqueous liquids including an acid-sensitive dye as described herein can also be used as a part of a multi-part dental composition. For example, a multi-part dental composition can include: a first part including an acid-sensitive dye; and a second part including an acid. Contacting the first part and the second part is effective to cause a color change. Thus, the color change provides an indication of when the first part and the second part of the multi-part dental composition have been contacted and/or mixed. Preferably, the color change is from colored to essentially colorless. Optionally, the second part includes a self-etching adhesive or a self-adhesive composition.

For the convenience of a practitioner, compositions used in methods of the present invention (e.g., aqueous liquids including an acid-sensitive dye) can be provided in kits. In one exemplary embodiment, the kit can include: a liquid including an acid-sensitive dye and water; and a dental etching composition. In another exemplary embodiment, the kit can include: a liquid including an acid-sensitive dye and water; and a self-etching dental adhesive. In another exemplary embodiment, the kit can include: a liquid including an acid-sensitive dye and water; and a self-adhesive dental composition.

Objects and advantages of this invention are further illustrated by the following examples, but the particular materials and amounts thereof recited in these examples, as well as other conditions and details, should not be construed to unduly limit this invention. Unless otherwise indicated, all parts and percentages are on a weight basis, all water is deionized water, and all molecular weights are weight average molecular weight.

EXAMPLES

Test Methods

Adhesion Shear Bond Strength to Enamel or Dentin Test Method

Adhesive shear bond strength to enamel or dentin for a given test sample was evaluated by the following procedure.

Preparation of Teeth. Bovine incisal teeth, free of soft tissue, were embedded in circular acrylic disks. The embedded teeth were stored in water in a refrigerator prior to use. In preparation for adhesive testing, the embedded teeth were ground to expose a flat enamel or dentin surface using 120-grit sandpaper mounted on a lapidary wheel. Further grinding and polishing of the tooth surface was done using 320-grit sandpaper on the lapidary wheel. The teeth were continuously rinsed with water during the grinding process. The polished teeth were stored in deionized water and used for testing within 2 hours after polishing. The teeth were allowed to warm in a 36° C. oven to between room temperature (23° C.) and 36° C. before use.

Teeth Treatment. An adhesive test sample was applied with a dental applicator brush over the entire surface of the prepared enamel or dentin surface according to the specific application techniques detailed in the Examples. After application, the adhesive coating was light cured for 10 seconds with an XL 3000 dental curing light (3M Company, St. Paul, Minn.). A 2.5-mm thick Teflon mold with a hole approximately 4.7 mm in diameter was clamped to the embedded tooth such that the hole in the mold exposed part of the adhesively prepared tooth surface. A composite material, A2 shade of FILTEK Z250 Universal Restorative (3M Company), was filled into the hole such that the hole was completely filled, but not overfilled, and light cured for 20 seconds to form a "button" that was adhesively attached to the tooth.

Adhesive Bond Strength Testing. The adhesive strength of a cured test example was evaluated by mounting the assembly (described above) in a holder clamped in the jaws of an INSTRON testing machine (Instron 4505, Instron Corp. Canton, Mass.) with the polished tooth surface oriented parallel to the direction of pull. A loop of orthodontic wire (0.44-mm diameter) was placed around the Z250 button adjacent to the polished tooth surface. The ends of the orthodontic wire were clamped in the pulling jaw of the INSTRON apparatus and pulled at a crosshead speed of 2 mm/min, thereby placing the adhesive bond in shear stress. The force in kilograms (kg) at which the bond failed was recorded, and this number was converted to a force per unit area (units of $kg/cm^2$ or MPa) using the known surface area of the button. Each reported value of adhesion to enamel or adhesion to dentin represents the average of 2 to 6 replicates.

Abbreviations, Descriptions, and Sources of Materials

| Abbreviation | Description and Source of Material |
|---|---|
| Rose Bengal | Acid-sensitive dye (Sigma-Aldrich, St. Louis, MO) |
| TEGDMA | Triethyleneglycol dimethacrylate (Sartomer, Exton, PA) |
| BisEMA-2 | Bisphenol A ethoxylate (2 EO/phenol) dimethacrylate (Sigma-Aldrich) |

-continued

| Abbreviation | Description and Source of Material |
|---|---|
| NPGDMA | Neopentylglycol dimethacrylate (Sigma-Aldrich) |
| MHP | Methacryloyloxyhexyl phosphate ($P_2O_5$ derived) (See Preparation Method described herein) |
| PM-2 | KAYAMER PM-2; Bis(methacryloxyethyl) phosphate (Nippon Kiyaku, Japan) |
| EDMAB | Ethyl 4-(N,N-dimethylamino)benzoate (Sigma-Aldrich) |
| DPIPF6 | Diphenyliodonium hexafluorophosphate (Johnson Matthey, Alpha Aesar Division, Ward Hill, NJ) |
| CPQ | Camphorquinone (Sigma-Aldrich) |
| TPA | Triphenyl antimony (Atofina Chemicals, Inc., Philadelphia, PA) |
| $ZrO_2$ Filler | Surface-treated zirconia filler (nano-sized primary particles) (See Preparation Method described herein) |
| RN-50 | NOIGEN RN-50 polymerizable nonionic surfactant (DAI-Ichi Kogyo Seiyaku Co. Ltd., Japan; William H. Minkema, MINK Inc., Plymouth, MN) |

Starting Materials Preparations

6-Methacryloxyhexyl Phosphate (MHP from $P_2O_5$)

6-Hydroxyhexyl Methacrylate Synthesis: 1,6-Hexanediol (1000.00 g, 8.46 mol, Sigma-Aldrich) was placed in a 1-liter 3-neck flask equipped with a mechanical stirrer and a narrow tube blowing dry air into the flask. The solid diol was heated to 90° C., at which temperature all the solid melted. With continuous stirring, p-toluenesulfonic acid crystals (18.95 g, 0.11 mol) followed by BHT (2.42 g, 0.011 mol) and methacrylic acid (728.49.02 g, 8.46 mol). Heating at 90° C. with stirring was continued for 5 hours during which time vacuum was applied using tap water aspirator for 5-10 minutes after each half-hour reaction time. The heat was turned off and the reaction mixture was cooled to room temperature. The viscous liquid obtained was washed with 10% aqueous sodium carbonate twice (2×240 ml), followed by washing with water (2×240 ml), and finally with 100 ml of saturated NaCl aqueous solution. The obtained oil was dried using anhydrous $Na_2SO_4$ then isolated by vacuum filtration to give 1067 g (67.70%) of 6-hydroxyhexyl methacrylate, a yellow oil. This desired product was formed along with 15-18% of 1,6-bis(methacryloyloxyhexane). Chemical characterization was by NMR analysis.

6-Methacryloxyhexyl Phosphate Synthesis: A slurry was formed by mixing $P_4O_{10}$ (178.66 g, 0.63 mol) and methylene chloride (500 ml) in a 1-liter flask equipped with a mechanical stirrer under $N_2$ atmosphere. The flask was cooled in an ice bath (0-5° C.) for 15 minutes. With continuous stirring, 6-hydroxyhexyl methacrylate (962.82 g, which contained 3.78 mol of the mono-methacrylate, along with its dimethacrylate by-product as described above) was added to the flask slowly over 2 hours. After complete addition, the mixture was stirred in the ice bath for 1 hour then at room temperature for 2 hours. BHT (500 mg) was added, and then the temperature was raised to reflux (40-41° C.) for 45 minutes. The heat was turned off and the mixture was allowed to cool to room temperature. The solvent was removed under vacuum to afford 1085 g (95.5%) of 6-Methacryloxyhexyl Phosphate as a yellow oil. Chemical characterization was by NMR analysis.

Surface-Treated $ZrO_2$ Filler

Zirconia Sol (217.323 g; 23.5% solids; Nalco, Naperville, Ill.) was weighed into a plastic flask and then added slowly with vigorous stirring to a solution of mono-2-(methacryloyloxy)ethyl succinate (28.796 g; Sigma-Aldrich) in 1-methoxy-2-propanol (200.001 g; Sigma-Aldrich) that was contained in a plastic flask. The resulting mixture was then dried at 90° C. to powder form (dryness) in a convection oven and subsequently ground with a mortar and pestle to a fine powder form for easier later redispersion. Average primary particle size of the zirconia filler was approximately 5 nm, with 50-75 nm loose agglomerates.

Example 1

Adhesive Application to Tooth and SBS Evaluations

An aqueous dye solution was prepared by dissolving Rose Bengal (7.5 mg) in water (5 g). A microbrush was used to apply the dye solution to a dry tooth surface such that the surface was a visible reddish/pink color. A dental adhesive composition (Adhesive Composition A, Table 1) was then applied by microbrush to the colored, wet tooth surface. Upon contact of the adhesive with the tooth surface, the surface changed in color from reddish/pink to colorless. The adhesive layer was dried, a second layer of adhesive (Adhesive Composition A) was applied to the dried tooth surface and lightly air-thinned. The tooth surface was then cured for 10 seconds and evaluated 16 hours post-cure for shear bond strength. The initial tooth preparation, curing conditions, and adhesive bond strength test procedures were as generally described in the Adhesion Shear Bond Strength to Enamel or Dentin Test Method described herein. The resulting SBS testing results were 26.8 MPa to enamel (average of 6 replicates) and 29.9 MPa to dentin (average of 2 replicates).

Similar SBS values were obtained in identical experiments using only water (no dye) as the initial application to the tooth surface. These results suggest that the presence of dye in the initial water coating has no effect on bond strength performance.

TABLE 1

| Adhesive Composition A | |
|---|---|
| Component | Amount (grams) |
| TEGDMA | 8.63 |
| BisEMA-2 | 4.31 |
| NPGDMA | 4.31 |
| MHP | 0.82 |
| PM-2 | 8.18 |
| EDMAB | 0.22 |
| DPIPF6 | 0.17 |
| CPQ | 0.28 |
| TPA | 0.01 |
| $ZrO_2$ Filler | 3.75 |
| RN-50 | 0.45 |

Example 2

Mixing of 2-Part Adhesive Composition

One part of the Rose Bengal aqueous dye solution as described in Example 1 was mixed with two parts of Adhesive Composition A (Table 1). As the two components were contacted and mixed together, the mixture color changed from a reddish/pink to essentially colorless. The color change can be indicative of the thoroughness of mixing. This example demonstrates that an acid-sensitive dye can serve as a contact or mixing indicator for an acidic component (e.g., a self-etching adhesive) and a second component that includes the dye.

Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A method of bonding a dental material to a dental structure, the method comprising:
   wetting a surface of a dental structure with a liquid comprising an acid-sensitive dye and water;
   applying a self-etching adhesive to at least a portion of the wet dental structure surface under conditions effective to cause a visually observable color change before hardening in the portion of the dental structure surface having the self-etching adhesive applied thereon;
   drying the dental structure surface to form an adhesive layer thereon;
   applying a dental material to the dental structure surface having the adhesive layer; and
   hardening at least one of the adhesive layer under conditions effective to form a bond between the dental material and the dental structure.

2. The method of claim 1 wherein the adhesive is hardened under conditions effective to form a bond between the dental material and the dental structure of at least 7 MPa.

3. The method of claim 1 wherein the adhesive is hardened before, during, or after applying the dental material.

4. The method of claim 1 wherein the dental material comprises a dental restorative, an orthodontic adhesive, an orthodontic appliance, or a combination thereof.

5. The method of claim 1 wherein conditions effective to cause a visually observable color change do not comprise exposure to a curing light.

6. A method of restoring a dental structure, the method comprising:
   wetting a surface of a dental structure with a liquid comprising an acid-sensitive dye and water;
   applying a self-adhesive composition to at least a portion of the wet dental structure surface under conditions effective to cause a visually observable color change before hardening in the portion of the dental structure surface having the self-adhesive composition applied thereon; and
   hardening the self-adhesive composition under conditions effective to form a bond between the hardened composition and the dental structure of at least 7 MPa.

7. The method of claim 6 wherein the self-adhesive composition comprises at least 40% by weight filler.

8. The method of claim 6 wherein conditions effective to cause a visually observable color change do not comprise exposure to a curing light.

9. A method of adhering an orthodontic appliance to a tooth, the method comprising:
   wetting a surface of a tooth with a liquid comprising an acid-sensitive dye and water;
   applying a self-adhesive composition to at least a portion of the wet tooth surface under conditions effective to cause a visually observable color change before hardening in the portion of the tooth surface having the self-adhesive composition applied thereon;
   applying an orthodontic appliance to the tooth surface having the self-adhesive composition applied thereon; and
   hardening the self-adhesive composition under conditions effective to form a bond between the orthodontic appliance and the tooth.

10. The method of claim 9 wherein the self-adhesive composition is a self-etching primer.

11. The method of claim 10 wherein the self-etching primer is applied using a transfer tray.

12. The method of claim 10 wherein the orthodontic appliance is precoated with an orthodontic adhesive.

13. The method of claim 9 wherein conditions effective to cause a visually observable color change do not comprise exposure to a curing light.

14. A method of adhering an orthodontic appliance to a tooth, the method comprising:
   wetting a surface of a tooth with a liquid comprising an acid-sensitive dye and water;
   applying an orthodontic appliance having a self-adhesive composition thereon to at least a portion of the wet tooth surface under conditions effective to cause a visually observable color change before hardening in the portion of the tooth surface having the orthodontic appliance and self-adhesive composition applied thereon; and
   hardening the self-adhesive composition under conditions effective to form a bond between the orthodontic appliance and the tooth.

15. The method of claim 14 further comprising applying a self-adhesive composition to an orthodontic appliance to provide the orthodontic appliance having the self-adhesive composition thereon.

16. The method of claim 14 wherein the orthodontic appliance having the self-adhesive composition thereon is provided as a precoated orthodontic appliance.

17. The method of claim 14 wherein conditions effective to cause a visually observable color change do not comprise exposure to a curing light.

18. A method for applying a composition to a dental structure, the method comprising:
   wetting a surface of a dental structure with a liquid comprising an acid-sensitive dye and water; and
   applying a composition to at least a portion of the wet dental structure surface under conditions effective to cause a visually observable color change before hardening in the portion of the dental structure surface having the composition applied thereon, wherein the composition is a self-etching adhesive, a self-adhesive composition, or a combination thereof.

19. The method of claim 18 wherein the visually observable color change is from colored to essentially colorless.

20. The method of claim 18 wherein the visually observable color change is from essentially colorless to colored.

21. The method of claim 18 wherein the visually observable color change is from a first color to a second color, wherein the second color is different than the first color.

22. The method of claim 18 wherein the acid-sensitive dye is selected from the group consisting of Rose Bengal, Bromothymol Blue, Methyl Red, Methyl Orange, Erythrosin B, Eosin Y, and combinations thereof.

23. The method of claim 18 wherein the liquid comprises 0.0001% to 5% by weight of the acid-sensitive dye.

24. The method of claim 18 wherein the liquid further comprises an antibacterial agent, a water soluble monomer, a pH adjuster agent, a buffer, a stabilizer, a surfactant, a fluoride anion, a fluoride releasing agent, or combinations thereof.

25. The method of claim 18 wherein the dental structure comprises enamel, dentin, or cementum.

26. The method of claim 18 wherein the self-etching adhesive is a non-aqueous self-etching adhesive.

27. The method of claim 26 wherein the non-aqueous self-etching adhesive comprises an ethylenically unsaturated compound with acid functionality, an ethylenically unsaturated compound without acid functionality, and an initiator system.

28. The method of claim 27 wherein the non-aqueous self-etching adhesive further comprises a filler.

29. The method of claim 27 wherein the acid-functionality comprises carboxylic acid functionality, phosphoric acid functionality, phosphonic acid functionality, sulfonic acid functionality, or combinations thereof.

30. The method of claim 27 wherein the non-aqueous self-etching adhesive further comprises a surfactant.

31. The method of claim 18 wherein the self-etching adhesive comprises a water-in-oil emulsion.

32. The method of claim 31 wherein the self-etching adhesive comprises an ethylenically unsaturated compound with acid functionality, an ethylenically unsaturated compound without acid functionality, an initiator system, and water.

33. The method of claim 32 wherein the self-etching adhesive further comprises a filler.

34. The method of claim 31 wherein the emulsion is physically stable.

35. The method of claim 31 wherein the self-etching adhesive comprises less than 30% by weight water.

36. The method of claim 31 wherein the emulsion is a water-in-oil micro-emulsion.

37. The method of claim 31 wherein the emulsion is chemically stable.

38. The method of claim 18 wherein the self-adhesive composition is a non-aqueous self-adhesive composition.

39. The method of claim 38 wherein the non-aqueous self-adhesive composition comprises an ethylenically unsaturated compound with acid functionality, an ethylenically unsaturated compound without acid functionality, an initiator system, and at least 40% by weight filler, based on the total weight of the non-aqueous self-adhesive composition.

40. The method of claim 38 wherein the self-adhesive composition is provided as a precoated orthodontic appliance, and the precoated orthodontic appliance is applied to the wet dental structure surface.

41. The method of claim 40 wherein the orthodontic appliance is selected from the group consisting of a bracket, a buccal tube, a band, a cleat, a button, a lingual retainer, a bite blocker, and combinations thereof.

42. The method of claim 40 wherein the self-adhesive composition is applied to a surface of an orthodontic appliance to provide a coated orthodontic appliance, and the coated orthodontic appliance is applied to the wet dental structure surface.

43. The method of claim 40 wherein the self-adhesive composition is provided on an adhesive transfer area of a substrate, and the self-adhesive composition is transferred from the adhesive transfer area of the substrate for applying to the orthodontic appliance.

\* \* \* \* \*

UNITED STATES PATENT AND TRADEMARK OFFICE
CERTIFICATE OF CORRECTION

PATENT NO.      : 8,465,284 B2
APPLICATION NO. : 11/571762
DATED           : June 18, 2013
INVENTOR(S)     : Bradley Dene Craig et al.

Page 1 of 1

It is certified that error appears in the above-identified patent and that said Letters Patent is hereby corrected as shown below:

In the Specification

Column 2
Line 4, Delete "Occurence," and insert -- Occurrence, --, therefor
Line 40, Delete "adhevise" and insert -- adhesive --, therefor.
Line 46, Delete ""Cetophosphonates" and insert -- "KetoPhosphonates --, therefor.
Line 48, Delete "Sufur" and insert -- Sulfur --, therefor.
Line 53, Delete "desclosing" and insert -- disclosing --, therefor.
Line 68, Delete "Catonic" and insert -- Cationic --, therefor.

Column 5
Line 20, Delete "Catonic" and insert -- Cationic --, therefor.

Column 11
Line 8, Delete "Kiyaku," and insert -- Kayaku, --, therefor.
Line 64, Delete "Ill.)" and insert -- Il.) --, therefor.

Signed and Sealed this
Sixth Day of May, 2014

Michelle K. Lee
*Deputy Director of the United States Patent and Trademark Office*